(12) United States Patent
Maher et al.

(10) Patent No.: US 7,749,775 B2
(45) Date of Patent: Jul. 6, 2010

(54) IMMUNOASSAY TEST DEVICE AND METHOD OF USE

(76) Inventors: Jonathan Scott Maher, 3051 Bullock La., Hebron, KY (US) 41048; Jeffrey A. Kraft, 3068 Inwood Dr., Cincinnati, OH (US) 45241; Kenneth J Kozak, 1007 Nottingham Dr., Cincinnati, OH (US) 45255

( * ) Notice: Subject to any disclaimer, the term of this patent is extended or adjusted under 35 U.S.C. 154(b) by 138 days.

(21) Appl. No.: 11/538,226

(22) Filed: Oct. 3, 2006

(65) Prior Publication Data

US 2008/0081341 A1 Apr. 3, 2008

(51) Int. Cl.
*G01N 33/53* (2006.01)

(52) U.S. Cl. .................. 436/518; 436/514; 436/527; 436/808; 436/810; 436/46; 436/165; 435/287.1; 435/287.2; 435/287.8; 435/5; 435/6; 435/7.1; 435/7.2; 435/7.92; 435/805; 435/970

(58) Field of Classification Search ............. 435/287.1, 435/5, 6, 7.1, 7.2, 7.92, 805, 970, 287.2, 435/287.8; 436/514, 518, 527, 808, 810, 436/46, 165; 422/56–61
See application file for complete search history.

(56) References Cited

U.S. PATENT DOCUMENTS

| | | | |
|---|---|---|---|
| 4,275,149 A | 6/1981 | Litman et al. | |
| 4,313,734 A | 2/1982 | Leuvering | |
| 4,703,017 A | 10/1987 | Campbell et al. | |
| 4,859,610 A | 8/1989 | Maggio et al. | |
| 4,885,240 A | 12/1989 | Wu | |
| 4,916,056 A | 4/1990 | Brown, III et al. | |
| 4,943,522 A | 7/1990 | Eisinger et al. | |
| 4,956,302 A | 9/1990 | Gordon et al. | |
| 4,956,392 A | 9/1990 | Saito et al. | |
| 5,008,080 A | 4/1991 | Brown, III et al. | |
| 5,051,237 A | 9/1991 | Grenner et al. | |
| 5,073,484 A | 12/1991 | Swanson et al. | |

(Continued)

FOREIGN PATENT DOCUMENTS

EP 250 137 B1 8/1992

(Continued)

OTHER PUBLICATIONS

U.S. Appl. No. 90/006,784, filed Sep. 26, 2003, Swanson, (On Appeal).

(Continued)

*Primary Examiner*—Bao-Thuy L Nguyen
(74) *Attorney, Agent, or Firm*—Frost Brown Todd LLC

(57) ABSTRACT

Disclosed is a diagnostic testing device that may be used to detect one or more analytes in a sample. The device comprises a receptacle and a holder for a test strip. The test strip may be, for example, a lateral flow test strip. The device and holder permit analysis of a sample, wherein the device is substantially sealed during testing and detection of results. To use, the holder containing a test strip is inserted into the receptacle containing sample to be analyzed. Capillary flow along the test strip is initiated by contact of the sample with the distal end of the test strip. The receptacle is such that results of the assay may be detected visually or using standard instrumentation such as by measuring light absorption or reflectance.

20 Claims, 6 Drawing Sheets

U.S. PATENT DOCUMENTS

| | | | |
|---|---|---|---|
| 5,075,078 A | 12/1991 | Osikowicz et al. | |
| 5,119,830 A | 6/1992 | Davis | |
| 5,120,643 A | 6/1992 | Ching et al. | |
| 5,149,622 A | 9/1992 | Brown et al. | |
| 5,160,701 A | 11/1992 | Brown, III et al. | |
| 5,198,368 A | 3/1993 | Khalil et al. | |
| 5,213,964 A | 5/1993 | Jones | |
| 5,252,459 A | 10/1993 | Tarcha et al. | |
| 5,252,496 A | 10/1993 | Kang et al. | |
| 5,409,832 A | 4/1995 | Pocock | |
| 5,415,994 A | 5/1995 | Imrich et al. | |
| 5,429,804 A | 7/1995 | Sayles | |
| 5,451,370 A | 9/1995 | Jones | |
| 5,504,013 A | 4/1996 | Senior | |
| 5,578,577 A | 11/1996 | Ching et al. | |
| 5,602,040 A | 2/1997 | May et al. | |
| 5,607,863 A | 3/1997 | Chandler | |
| 5,622,871 A | 4/1997 | May et al. | |
| 5,654,162 A | 8/1997 | Guire et al. | |
| 5,655,503 A | 8/1997 | Kampichler et al. | |
| 5,656,502 A * | 8/1997 | MacKay et al. | 436/180 |
| 5,656,503 A | 8/1997 | May et al. | |
| 5,658,723 A | 8/1997 | Oberhardt | |
| 5,670,381 A | 9/1997 | Jou et al. | |
| 5,686,315 A | 11/1997 | Pronovost et al. | |
| 5,686,316 A | 11/1997 | Fiechtner et al. | |
| 5,712,172 A | 1/1998 | Huang et al. | |
| 5,714,389 A | 2/1998 | Charlton et al. | |
| 5,750,333 A | 5/1998 | Clark | |
| 5,766,961 A | 6/1998 | Pawlak et al. | |
| 5,770,460 A | 6/1998 | Pawlak et al. | |
| 5,795,784 A | 8/1998 | Arnquist et al. | |
| 5,798,273 A | 8/1998 | Shuler et al. | |
| 5,869,003 A | 2/1999 | Nason | |
| 5,922,537 A | 7/1999 | Ewart et al. | |
| 5,989,921 A | 11/1999 | Charlton et al. | |
| 6,020,147 A | 2/2000 | Guire et al. | |
| 6,132,682 A | 10/2000 | Christner et al. | |
| 6,136,549 A | 10/2000 | Feistel | |
| 6,187,598 B1 | 2/2001 | May et al. | |
| 6,194,221 B1 | 2/2001 | Rehg et al. | |
| 6,228,660 B1 | 5/2001 | May et al. | |
| 6,297,020 B1 | 10/2001 | Brock | |
| 6,352,862 B1 | 3/2002 | Davis et al. | |
| 6,365,417 B1 | 4/2002 | Fleming et al. | |
| 6,372,514 B1 * | 4/2002 | Lee | 436/518 |
| 6,372,516 B1 * | 4/2002 | Sun | 436/518 |
| 6,403,383 B1 * | 6/2002 | Casterlin et al. | 436/518 |
| 6,432,358 B2 | 8/2002 | Norris et al. | |
| 6,514,769 B2 * | 2/2003 | Lee | 436/518 |
| 6,534,320 B2 | 3/2003 | Ching et al. | |
| 6,565,808 B2 | 5/2003 | Hudak et al. | |
| 6,576,193 B1 | 6/2003 | Cui et al. | |
| 6,616,894 B2 | 9/2003 | Lappe et al. | |
| 6,623,701 B1 | 9/2003 | Eichele et al. | |
| 6,627,152 B1 | 9/2003 | Wong | |
| 6,656,744 B2 | 12/2003 | Pronovost et al. | |
| 6,663,835 B2 | 12/2003 | Allen et al. | |
| 6,669,908 B2 | 12/2003 | Weyker et al. | |
| 6,680,027 B2 | 1/2004 | Kang et al. | |
| RE38,430 E | 2/2004 | Rosenstein | |
| 6,730,268 B2 | 5/2004 | Lee et al. | |
| 6,740,293 B1 | 5/2004 | Deng | |
| 6,767,710 B2 | 7/2004 | DiNello et al. | |
| 6,818,455 B2 | 11/2004 | May et al. | |
| 6,824,975 B2 | 11/2004 | Hubscher et al. | |
| 6,844,200 B2 | 1/2005 | Brock | |
| 6,875,185 B2 * | 4/2005 | Wong et al. | 600/584 |
| 6,881,581 B2 | 4/2005 | Jones et al. | |
| 6,890,484 B2 | 5/2005 | Bautista et al. | |
| 6,979,576 B1 | 12/2005 | Cheng et al. | |
| 6,998,273 B1 | 2/2006 | Fleming et al. | |
| 7,109,042 B2 | 9/2006 | May et al. | |
| 7,294,502 B2 * | 11/2007 | Eckermann et al. | 435/287.1 |
| 7,374,951 B2 * | 5/2008 | Ash et al. | 436/518 |
| 7,413,880 B2 * | 8/2008 | Aki et al. | 435/100 |
| 2001/0048893 A1 | 12/2001 | Norris et al. | |
| 2002/0001818 A1 | 1/2002 | Brock | |
| 2002/0119486 A1 | 8/2002 | Oberhardt | |
| 2003/0021727 A1 | 1/2003 | Weyker et al. | |
| 2003/0039583 A1 | 2/2003 | Miller et al. | |
| 2003/0049857 A1 | 3/2003 | Chan | |
| 2003/0166291 A1 | 9/2003 | Jones et al. | |
| 2003/0224471 A1 | 12/2003 | Jones et al. | |
| 2004/0002063 A1 | 1/2004 | Chan et al. | |
| 2004/0018634 A1 | 1/2004 | Hajizadeh et al. | |
| 2004/0184954 A1 | 9/2004 | Guo et al. | |
| 2004/0235182 A1 | 11/2004 | Jones | |
| 2005/0023672 A1 | 2/2005 | Oostman et al. | |
| 2005/0047972 A1 | 3/2005 | Lauks et al. | |
| 2005/0112023 A1 | 5/2005 | Liang | |
| 2005/0112024 A1 | 5/2005 | Guo et al. | |
| 2005/0112785 A1 | 5/2005 | Wong et al. | |
| 2005/0124077 A1 | 6/2005 | Cole et al. | |
| 2005/0130293 A1 | 6/2005 | Blatt et al. | |
| 2005/0164404 A1 | 7/2005 | Marlborough et al. | |
| 2005/0181521 A1 | 8/2005 | Niskanen et al. | |
| 2005/0208593 A1 | 9/2005 | Vail et al. | |
| 2005/0208609 A1 | 9/2005 | Jones et al. | |
| 2005/0221502 A1 | 10/2005 | Shindelman et al. | |
| 2005/0244986 A1 | 11/2005 | May et al. | |
| 2005/0277163 A1 | 12/2005 | Cheng et al. | |
| 2005/0277202 A1 | 12/2005 | Fleming et al. | |
| 2006/0024843 A1 | 2/2006 | Lee et al. | |
| 2006/0029517 A1 | 2/2006 | Hartselle | |
| 2006/0210451 A1 | 9/2006 | Anderson et al. | |

FOREIGN PATENT DOCUMENTS

| | | |
|---|---|---|
| EP | 0348006 B1 | 12/1993 |
| EP | 0348006 B2 | 10/1997 |
| EP | 0712495 B1 | 10/2001 |
| EP | 0260965 B2 | 1/2002 |
| EP | 1329724 A2 | 6/2005 |
| EP | 1329724 A3 | 6/2005 |
| EP | 1329724 B1 | 6/2005 |
| EP | 1566640 A1 | 8/2005 |
| EP | 1357383 A1 | 9/2005 |
| EP | 1357383 B1 | 9/2005 |
| GB | 2342992 A | 4/2000 |
| WO | WO 93/07292 | 4/1993 |
| WO | WO 9504280 A1 | 2/1995 |
| WO | WO 96/40434 | 12/1996 |
| WO | WO 98/55233 A1 | 12/1998 |
| WO | WO 0025135 A1 | 5/2000 |
| WO | WO 01/29558 | 4/2001 |
| WO | WO 02/095396 A3 | 11/2002 |
| WO | WO 03/004609 | 1/2003 |
| WO | WO 03/012443 A3 | 2/2003 |
| WO | WO 03/016902 A1 | 2/2003 |
| WO | WO 03/050537 A1 | 6/2003 |
| WO | WO 03/061569 A2 | 7/2003 |
| WO | WO 03/087401 A1 | 10/2003 |
| WO | WO 03/098215 A1 | 11/2003 |
| WO | WO 2004/038364 A3 | 5/2004 |
| WO | WO 2004/090555 A1 | 10/2004 |
| WO | WO 2005/044110 A1 | 5/2005 |
| WO | WO 2005/078441 A1 | 8/2005 |
| WO | WO 2005/098442 A2 | 10/2005 |

| | | | |
|---|---|---|---|
| WO | WO 2005/119253 A1 | 12/2005 | |
| WO | WO 2005/124347 A1 | 12/2005 | |

OTHER PUBLICATIONS

U.S. Appl. No. 07/609,794, filed Nov. 6, 1990, Guire, (Abandoned).
U.S. Appl. No. 07/574,607, filed Aug. 28, 1990, Guire, (Abandoned).
Arens, M.Q., et al., "Preclinical and Clinical Performance of the Efoora Test, a Rapid Test for Detection of Human Immunodeficiency Virus-Specific Antibodies", Journal Of Clinical Microbiology, May 2005, pp. 2399-2406, vol. 43, No. 5, American Society for Microbiology.
Fernandez-Sanchez, C., et al., "One-step immunostrip test for the simultaneous detection of free and total prostate specific antigen in serum", Journal Of Immunological Methods, 2005, pp. 1-12, 307, Elsevier.
Fernandez-Sanchez, C., et al., "Quantitative impedimetric immunosensor for free and total prostate specific antigen based on a lateral flow assay format", Electrochemistry Communications, 2004, pp. 138-143, vol. 6, Science Direct.
Johnston, S., et al., "Evaluation of Three Commercial Assays for Detection of Giardia and Cryptosporidium Organisms in Fecal Specimens", Journal of Clinical Microbiology, Feb. 2003, pp. 623-626, vol. 41, No. 2, American Society for Microbiology.
Ketema, F., et al., "Assessment of the Performance of a Rapid, Lateral Flow Assay for the Detection of Antibodies to HIV", Journal Of Acquired Immune Deficiency Syndromes, May 2001, pp. 63-70, vol. 27, No. 1, Lippincott Williams & Wilkins, Inc.
Kim, S., et al., "Development of a Test Strip Reader for a Lateral Flow Membrane-based Immunochromatographic Assay", Biotechnology and Bioprocess Engineering, 2004, pp. 127-131, vol. 9, KSBB.
Myers, M.J., et al., "Evaluation of Two Commercial Lateral-Flow Test Kits for Detection of Animal Proteins in Animal Feed", Journal of Food Protection, 2005, pp. 2656-2664, vol. 68, No. 12, International Association for Food Protection.
Salomone, A., et al., "Reliability of Detection of Citrus Tristeza Virus By An Immunochromatographic Lateral Flow Assay in Comparison with ELISA", Journal of Plant Pathology, 2004, pp. 43-48, vol. 86, No. 1, Edizioni ETS Pisa.
Slinger, R., et al., "Evaluation of the QuickLab RSV Test, a New Rapid Lateral-Flow Immunoassay for Detection of Respiratory Syncytial Virus Antigen", Journal of Clinical Microbiology, Aug. 2004, pp. 3731-3733, vol. 42, No. 8, American Society for Microbiology.
Takada, K., et al., "New Rapid Polymerase Chain Reaction-Immunochromatographic Assay for Porphyromonas Gingivalis", Journal of Periodontology, pp. 508-512, vol. 76, No. 4, United States.
Product Information for ACON International.
Product Information for BinaxNOW, Influenza A&B, (reviewed Mar. 23, 2005).
Product Information for Quick Vue Influenza Test.
New Zealand Office Action dated Nov. 18, 2008 for Application No. 560565.
EP Search Report dated Jan. 31, 2008 for Application No. 07019359.4.

* cited by examiner

IMMUNOASSAY TEST DEVICE AND METHOD OF USE

BACKGROUND OF THE INVENTION

Disclosed is a novel device for detection of an analyte in a sample using a lateral flow assay. The device and method of the present invention may be easily and inexpensively assembled, and suitable for use by personnel with little specialized training. The device further provides for sanitary handling and disposal of biological samples. The device and method disclosed herein may be used with labels conventionally used with lateral flow assays such as colloidal metals, or may also be used with colorimetric or fluorescent labels that require instrumentation for detection.

Immunoassays

The present invention relates to assays utilizing test strips, in particular, a lateral flow immunoassay. The immunoassay, in general, is a sensitive technique used to measure levels of a substance using the reaction of an antibody or antibodies to its antigen. Immunoassays generally rely on binding of an antibody to an antigen. Monoclonal antibodies, in particular, are often used because such antibodies generally bind to only one site of a particular molecule. This specific binding enhances the specificity and accuracy of binding to a particular analyte. The antibodies used in immunoassays typically have a high affinity for the antigen such that a high proportion of the antigen binds to the antibody.

Immunoassays are powerful and versatile biomedical diagnostic tools that can be used, for example, to monitor drug and hormone levels in body fluids, diagnose infectious and autoimmune diseases, and diagnose and monitor treatment of cancer.

One analyte in particular that is ideally suited for detection using immunoassay techniques is influenza. Influenza is a highly contagious epidemic to pandemic acute viral respiratory disease caused by several genera of the Orthomyxoviridae family. Influenzavirus A and Influenzavirus B are the two genera most commonly associated with disease in humans. Influenza infection rates tend to be highest in pediatric populations, while serious complications from influenza disease are more common in the elderly. Clinical signs and symptoms begin after a 1-4 day incubation period and include cough, fever, myalgia and malaise. The clinical presentation of influenza can range from asymptomatic infection to fatal pneumonia. Influenza co-circulates with other respiratory pathogens; hence it is important to differentiate influenza from other respiratory diseases. Rapid influenza detection tests facilitate the more timely administration of antiviral drugs, which, in general, are of clinical benefit when administered within 48 hours of the appearance of symptoms. Not all antiviral drugs are effective against both influenza A and influenza B; therefore it is important to distinguish between the two.

Influenza A and B can be detected in human respiratory samples by a variety of methods including tissue culture, immunofluorescent assay and enzyme immunoassay. Tissue culture isolation remains the gold standard for the detection of influenza, yet the procedure can take up to 7 days to complete. Immunofluorescent antibody-based tests are moderately sensitive, yet highly dependent on specimen quality and preparation. The rapid detection of influenza using enzyme and microparticle-based immunoassays has become an important aspect of patient management in patients of all ages with acute respiratory disease due to influenza. Test results can be used to support data available from the patient's clinical evaluation and assist the physician in determining the course of action.

Immunoassay techniques typically employ a detectable label that permits the user to determine whether the analyte is present in the sample. The label can be conjugated to a particle such as an antibody that binds to the analyte (referred to herein as a first "binding reagent"). The type of label used may vary, and may include visually detectable labels as well as labels that require instrumentation for detection. Non-limiting examples of labels that can be used with immunoassay techniques include enzymes, radioisotopes, fluorescent tags, carbon particles, beads, or metal sol tags such as colloidal gold.

Lateral Flow Immunoassays

Lateral flow assays (or "flow-through" assays) are well known in the art and are described in Ching et al., U.S. Pat. No. 6,534,320, May et al., U.S. Pat. No. 6,228,660, Charlton et al, U.S. Pat. No. 5,989,921, Charlton U.S. Pat. No. 6,485,982, Charlton U.S. Pat. No. 5,714,389, Rosenstein, U.S. RE 38,430 all incorporated herein by reference.

Lateral flow assays are characterized in that a liquid solution containing an analyte to be detected is transported by capillary action laterally along a membrane strip. The membrane strip typically has reagents impregnated in the membrane. Sample is applied to one end of the strip (typically at a first absorbent pad) and sometimes with the aid of a solvent such as water. The sample may be mixed with a labeling reagent having a first binding reagent before contact with the strip, or the strip may contain labeling reagent therein. As the liquid passes through a "detection zone," second binding reagents immobilized on the strip permit visualization of the assay results. The lateral flow assay is typically rapid and provides sensitive and accurate detection of analytes, depending in part on the selection of the binding reagents used.

Lateral flow assays may employ "competitive" or "non-competitive" techniques, both of which are well-known in the art. In the competitive-type immunoassay, analyte in a sample is mixed with analyte that is conjugated to a detectable label. The mixture is then contacted with a lateral flow test strip. The mixture then migrates along a flow path defined by a membrane. The unlabeled analyte (from the sample) and labeled analyte compete for a limited number of binding sites on a binding agent immobilized on the test strip. The amount of labeled analyte detected at the detection region in a competitive assay is inversely proportional to the concentration of analyte in the sample (i.e., a greater amount of accumulated label indicates lower levels of analyte in the test sample).

In contrast, in "non-competitive" or "sandwich"-type immunoassays, antigen in the sample binds to a first binding reagent (such as an antibody) conjugated to a label (the "labeling reagent"). The sample containing antigen bound to the labeling reagent is then contacted with a lateral flow assay test strip. As the mixture migrates by capillary action along the membrane, the analyte-labeling reagent complex contacts and binds to a second binding reagent immobilized in the membrane. The label-analyte complex accumulates on the membrane, and a visible indicator line results. The amount of accumulated label is directly proportional to the concentration of the antigen in the sample. Both competitive-type and non-competitive-type assays are described in Ching et al, U.S. Pat. No. 6,534,320, incorporated herein by reference.

The lateral flow immunoassays typically employ the same basic components. These are described in, for example, Ching et al, U.S. Pat. No. 6,534,320 and May et al. U.S. Pat. No. 6,228,660. These components are: a first absorbent material, a membrane (such as nitrocellulose), and a second absorbent material, wherein the test strip has reagents impregnated therein for the detection of analytes.

Lateral flow devices can also be categorized as using either a one-step or two-step method. The two-step method (also referred to as the "pour on" method) is described in European Patent Application 0 250 137 A2, entitled "Colloidal Gold Immunoassay," published Dec. 12, 1987 ("Mochnal"). In this method, the sample and labeling reagent are mixed prior to contacting the sample with the lateral flow test strip. After mixing sample with labeling reagent, the mixture is contacted with a first absorbent material to initiate the lateral flow assay. The sample then flows along the membrane, contacting one or more immobilized second binding reagents. Analyte in the sample binds to the second binding reagent and accumulated label results in a visible reaction. The two-step method is characterized by the initial step of pre-mixing liquid sample with labeling reagent prior to contacting the mixture to the test strip.

In contrast, in the "dried-on" or "one-step" method, sample is not mixed with labeling reagent prior to contacting a test strip. In the one-step method, the labeling reagent is pre-dried and embedded within the test strip, typically within the first absorbent pad. Liquid sample applied directly to the first absorbent pad solubilizes the dried labeling reagent. As the liquid sample flows laterally along the test strip towards the test site, analyte binds to and transports the labeling reagent bound to analyte to an immobilized second binder. As in the two-step method described above, the analyte reacts with a second binding reagent immobilized on the matrix to effect a visual result. The one-step method is distinct from the two-step method primarily in that all of the reagents necessary for the assay are present in dry form on the test strip, eliminating the need for a separate mixing step.

Additionally, cross-contamination and sanitation is often a concern in the use of lateral flow assays. Test strips used for detection of analytes in biological samples, such as urine, saliva or feces, pose a potential contamination hazard when the test strips are contacted with sample and then transported to a different location. Contamination can occur when the test strips are in use, or upon disposal of the strips. As such, it is desirable to have a device that provides sanitary handling and disposal, minimizing cross contamination of test strips or personnel.

The invention described herein provides a support for a test strip, in particular, a lateral flow immunoassay test strip, and a device for conducting assays using test strips, that provide for improved ease of use, assembly, sanitary handling and disposal. The invention further relates to a device that may be used for detection of multiple labeling reagents including those that emit light or that require the use of instrumentation such as spectrophotometers.

BRIEF SUMMARY OF THE INVENTION

Disclosed herein is a device for determining the presence or absence of an analyte in a sample, wherein the device comprises a receptacle, a holder, and a test strip. In one embodiment, the holder comprises an elongated region for affixing a test strip, a stop feature, a closure for the receptacle, a grip member, an alignment feature and retention features. The holder may further comprise secondary pins for securing the test strip.

In another embodiment, the holder comprises a grip member, a stop feature, a closure, an alignment feature, and a hinge wherein the grip member and closure are formed by folding the top portion of the grip member upon the lower portion of the grip member at the hinge Another embodiment of the present invention is further related to a device for determining the presence or absence of an analyte in a sample, the device comprising a receptacle containing a labeling reagent that binds with the analyte and a holder. In one embodiment, the holder contains a test strip comprising a first absorbent pad, a membrane strip and a second absorbent pad defining a flow path for transporting a liquid sample, the test strip having at least one detection region. The test strip is held in a recess within the holder which further comprises an elongated support containing the recess and having an alignment feature, a closure, a stop feature and a grip member. In one embodiment, the holder is formed by folding the top of the unassembled (unfolded) holder at a hinge such that the top portion of the grip member is folded upon the lower portion of the grip member thereby capturing the second absorbent pad of the test strip between the two surfaces of the grip member of the holder. The holder also comprises a closure that substantially seals the receptacle when the holder is inserted into the receptacle.

The device may be provided in the form of a kit containing 1) a receptacle containing the dried and dispensed gold conjugate, 2) a holder and strip assembly, 3) a swab or transfer pipette and (in a four-part embodiment) 4) a rack or other assembly for maintaining the device in an upright position during testing.

Described herein are various embodiments of the invention, one or more examples of which are set forth below. Each example is provided by way of explanation, and not limitation, of the invention. It will be apparent to those skilled in the art that modifications may be made in the present invention without departing from the scope or spirit of the invention. Thus, it is intended that the present invention covers such modifications and variations as come within the scope of the claims and their equivalents.

BRIEF DESCRIPTION OF THE DRAWING

The invention will now be illustrated with respect to the following drawings illustrating embodiments of the invention in which.

DETAILED DESCRIPTION OF THE INVENTION

Definitions

Figure 1:
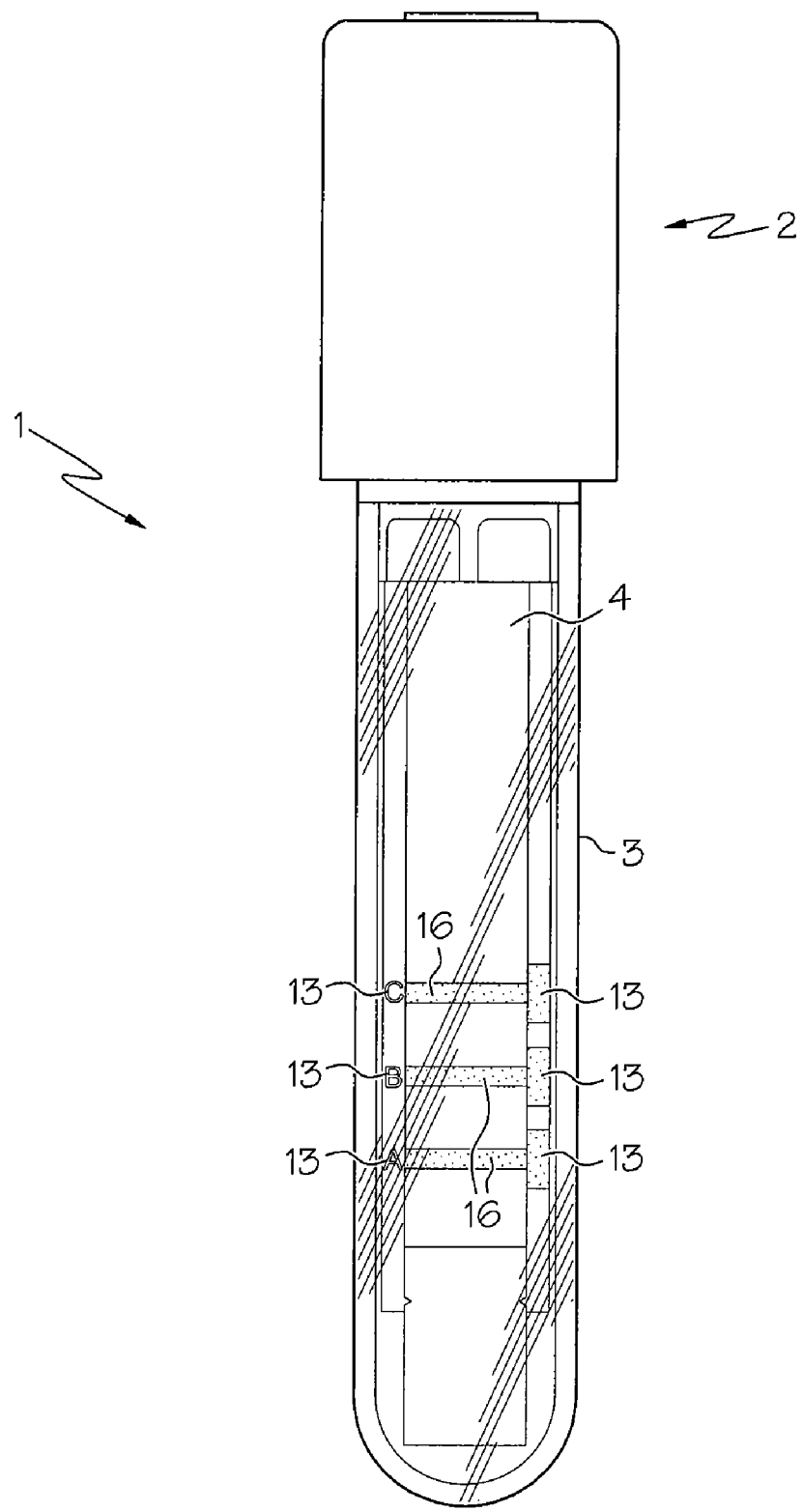
FIG. 1 is a front view of an embodiment of the invention.

The singular forms "a", "an", and "the" include plural references unless the context clearly dictates otherwise.

As used herein, the term "analyte" generally refers to a substance to be detected. For instance, analytes may include antigenic substances, haptens, antibodies, and combinations thereof. The analyte may be any analyte described in the art.

An "analyte detection region" or "detection region" is any region of an assay device in which the analyte or label may be detected and/or measured to determine the presence or absence of analyte in a sample. The analyte detection region may be qualitative or quantitative in nature. Thus in a lateral flow device, for example, the analyte detection region may be part of a porous matrix which contains binding reagents for immobilizing a detectable label. One or more detection regions may be present. Depending on the assay format, the amount of immobilized label in the analyte detection region may increase or decrease in the presence of analyte. For example, in a sandwich assay format, the amount of immobilized label will increase, while in a competition assay format, the amount of immobilized label will decrease.

The term "emission signal" refers to electromagnetic radiation emitted when an atom in an excited higher energy state decays to a lower energy state.

The term "excitation signal" refers to the energy, for example, that form electromagnetic radiation, which causes an electron of an atom to move from a lower energy state into an "excited" higher energy state.

The term "label" as used herein refers to any substance that is capable of producing a detectable signal, whether visibly or by using suitable instrumentation. Various labels suitable for use in the present invention include, but are not limited to, chromatogens, fluorescent or chemiluminescent compounds, catalysts, enzymes, enzymatic substrates, dyes, colloidal metallic and nonmetallic particles, and organic polymer latex particles.

The term "luminescence" refers to any emission of light that does not derive energy from the temperature of an energy source (for example, a source of electromagnetic radiation, a chemical reaction, mechanical energy). In general, the source causes an electron of an atom to move from a lower energy state into an "excited" higher energy state; then the electron releases that energy in the form of emitted light when it falls back to a lower energy state. Such emission of light usually occurs in the visible or near-visible range of the electromagnetic spectrum. The term "luminescence" includes, but is not limited to, such light emission phenomena such as phosphorescence, fluorescence, bioluminescence, radioluminescence, electro-luminescence, and thermo-luminescence.

The term "luminescent label" refers to a label that generates a luminescent signal, e.g. an emission of light that does not derive energy from the temperature of the emitting source. The luminescent label may be, for example, a fluorescent molecule, a phosphorescent molecule, a radiluminescent molecule, a luminescent chelate, a phosphor or phosphor-containing compound, or a quantum dot.

As used herein, the term "porous material" refers to any material capable of providing capillary action. This would include material such as, for example, nitrocellulose, nitrocellulose blends with polyester or cellulose, untreated paper, porous paper, rayon, glass fiber, acrylonitrile copolymer, or nylon. One skilled in the art will have knowledge of other porous materials that allow lateral flow.

As used herein, the term "test sample" generally refers to a biological material suspected of containing an analyte. The test sample may, for instance, include materials obtained directly from a source, as well as materials pretreated using techniques, such as, but not limited to, filtration, precipitation, dilution, distillation, mixing, concentration, inactivation of interfering components, the addition of reagents, lysing, and so forth. The test sample may be obtained or derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium or to release the analyte.

As used herein, the term "detection zone" when used to refer to a test strip, refers to the region on the membrane containing binding reagents, whether binding to molecules that indicate a positive or negative control, or to molecules that indicate presence or absence of analyte. The binding reagents may include those that bind to analyte, labeling reagent, label, or any other molecules such that a visual signal is obtained.

Test Device

Figure 2:
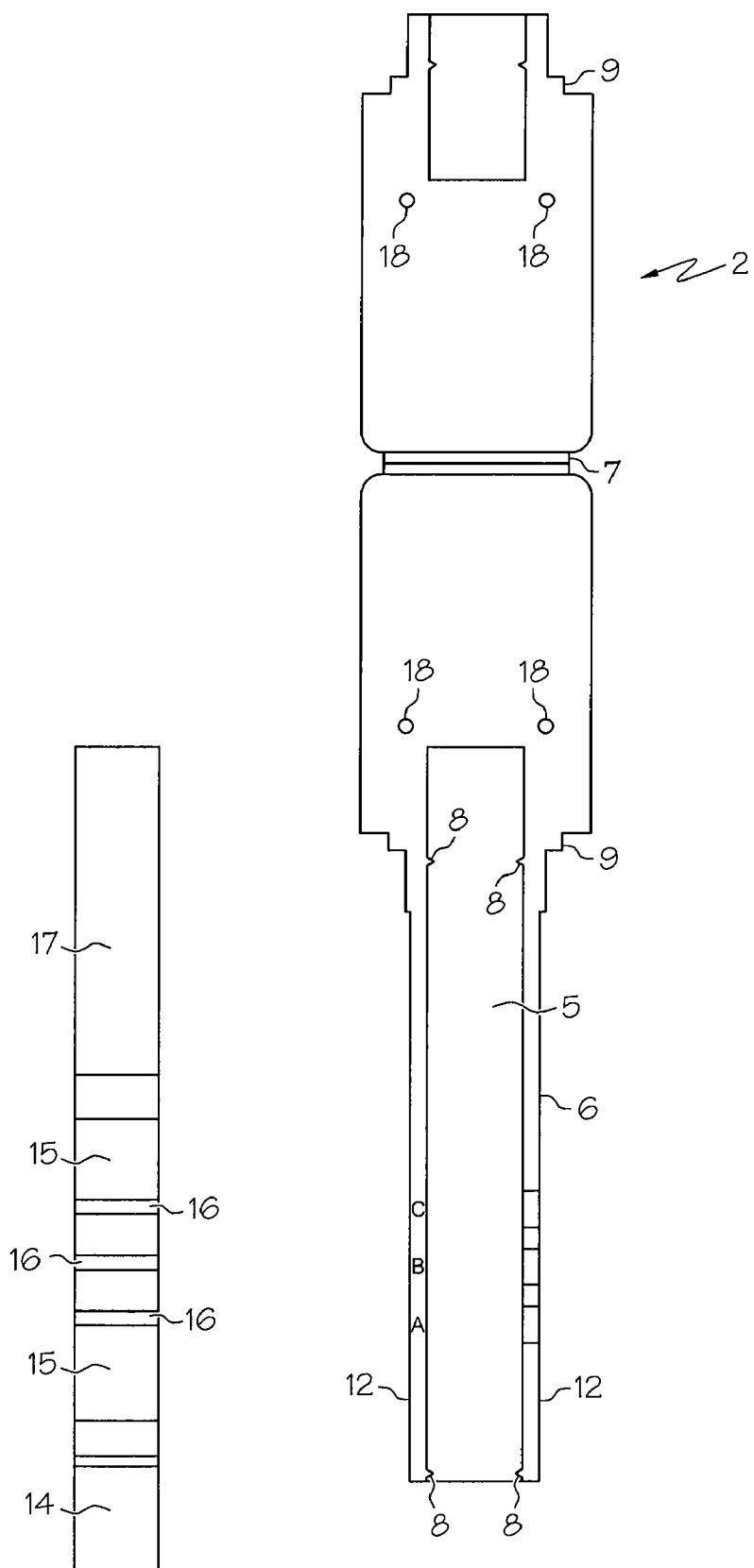
FIG. 2 is an exploded view of the unassembled holder and test strip.
Figure 8:
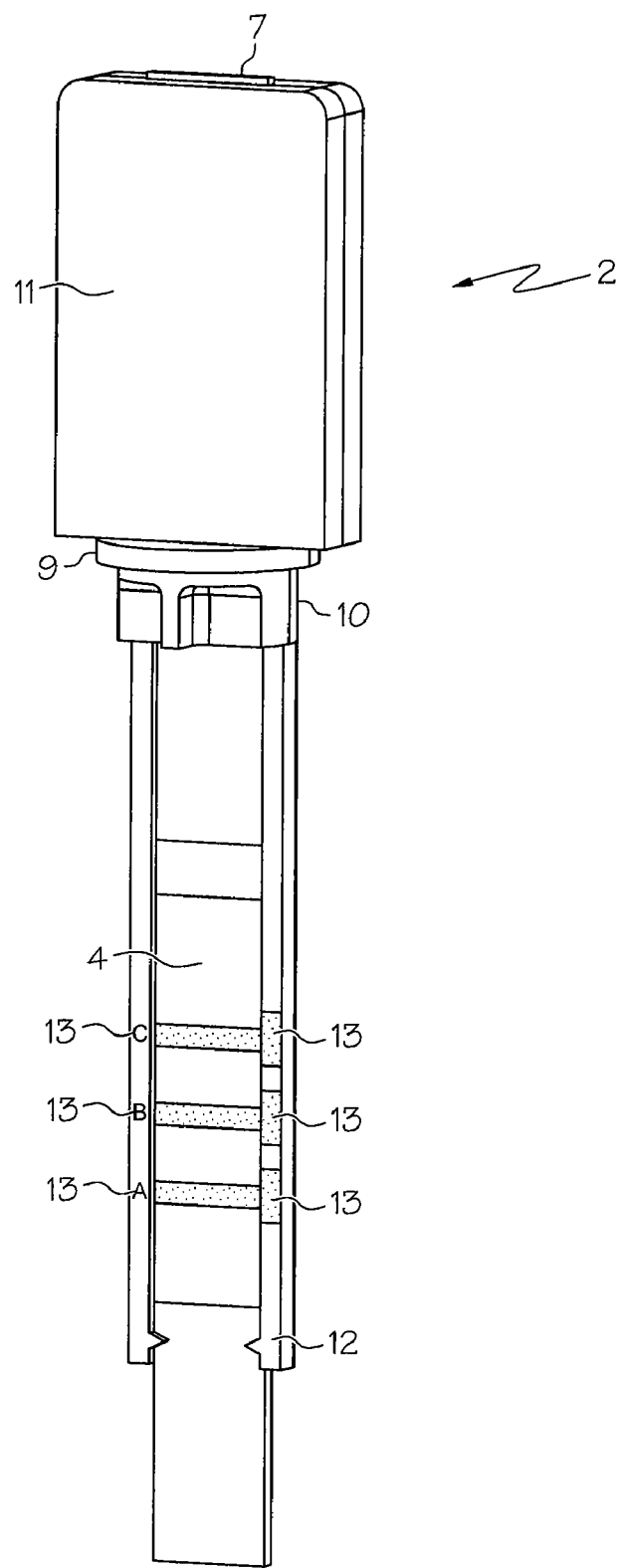
FIG. 8 is a perspective view of the holder.

FIG. 1 depicts one embodiment of the present invention. In this embodiment, the test device 1 comprises a receptacle 3, a holder 2, and a test strip 4 wherein the test strip 4 allows fluids to flow laterally along its length. The test may be any test strip known in the art. The receptacle 3 may be used to receive sample, diluent and/or labeling reagent. The holder 2 is used to hold any suitable test strip 4 known in the art, such as a lateral flow immunoassay test strip as shown in FIGS. 1, 2 and 8.

The Receptacle

As shown in FIG. 1, the receptacle 3 of the device 1 generally has an elongated shape that may be rounded on the bottom (having a test-tube like shape, as shown) or flattened (not shown). Where the bottom of the receptacle 3 is flattened, the receptacle 3 may be self-standing.

The receptacle 3 may also be cuvette-shaped or having the properties of a cuvette such that the receptacle 3 is compatible for use with spectrophotometric instruments or the like. However, the receptacle 3 may be of any shape suitable to receive both sample and the holder 2.

In embodiments in which the receptacle 3 has the properties of a cuvette, the receptacle 3 may have a cuvette-like shape such as, for example, cuvettes provided by Ocean Optics Inc. CVD-UV and CVD-VIS Disposable Cuvettes, manufactured and sold by Ocean Optics Inc., are plastic cuvettes that work in the UV range—transmitting light between 220-900 nm. The CVD-VIS Cuvettes transmit light from 350-900 nm and are suited for use in VIS applications. The cuvette may be square or triangular in shape. Any cuvettes known in the art can be used with the present invention.

In embodiments using a receptacle 3 having cuvette-like properties, the receptacle 3 can be used with labeling reagents that use fluorescent or other luminescent labels, and can be used in conjunction with spectrofluorometers, for example, without the need to transfer sample to a second container. In this embodiment, the sample need not be removed from the receptacle 3 to determine, for example, light absorption or refraction. The holder 2 may or may not be removed prior to evaluation or detection. Where removed prior to evaluation or detection, the receptacle 3 may be closed with any cap known to seal a cuvette or test tube (not shown).

In embodiments using a test-tube shaped receptacle 3, the receptacle 3 may be shaped to allow use with a vortexing machine having a test-tube shaped cup, and may be compatible with standard test-tube racks that can maintain the device in an upright position during use.

Regardless of the shape, receptacle 3 of device 1 may be manufactured from glass, plastic or any other material suitable for use with the analyte, or any diluent, etc. The receptacle 3 may be comprised of a material that provides chemical resistance, permitting use with organic solvents, as well as acids and bases.

The receptacle 3 may be wholly or partly transparent to visible light, or may be wholly or partly opaque. In some embodiments, the receptacle 3 may be opaque, with the exception of viewing windows on the receptacle 3. The viewing windows may take a variety of different shapes, and may be present at varied locations on the receptacle 3, depending on the desired use of the device, and the nature of the labels.

For example, where visually detectable labels are used with the device, the viewing windows in the receptacle 3 may be positioned such that the detection regions of the test strip are visible through the windows when holder 2 is placed in receptacle 3. Alternatively, the windows may be placed such that light reflectance or absorption of a sample may be measured using appropriate instrumentation.

In a further embodiment, receptacle 3 may be shaped in a manner that provides magnification of the contents or test strip 4 therein. For example, a portion of receptacle 3 may be curved or suitably shaped to magnify the regions of an enclosed test strip 4 such that viewing of the accumulated label is enhanced.

The receptacle 3 may be shaped so that it can be used with test tube or cuvette racks available, or may be used with specially-designed racks that maintain the device in an upright position during use. Such a specially designed rack may be provided to the end-user as part of a kit, described below.

The receptacle 3 used in the device 1 disclosed herein may be disposable or may be able to be reused.

It should be understood that receptacle 3 is such that a user may use both a lateral flow assay test strip to analyze the sample along with other methods to analyze the sample. For example, the test strip 4 may be used and removed, then the remaining sample may be assayed using other methods known in the art.

Holder

As shown in FIGS. 1, 2 and 8, the holder 2 of device 1 is used to hold a lateral flow test strip 4. Holder 2 is shaped to perform one or more of the following functions: 1) substantially seal the receptacle 3; 2) provide a support structure for the test strip 4; 3) provide a means for positioning the test strip 4 relative to the receptacle 3 and sample; 4) minimize contamination of sample and personnel; 5) minimize contamination of the test strip 4 when manipulating or inserting the holder 2 into the receptacle 3, and; 6) provide one or more detection guides 13 ("reading guides") for detection of results on the test strip 4.

Figure 3:
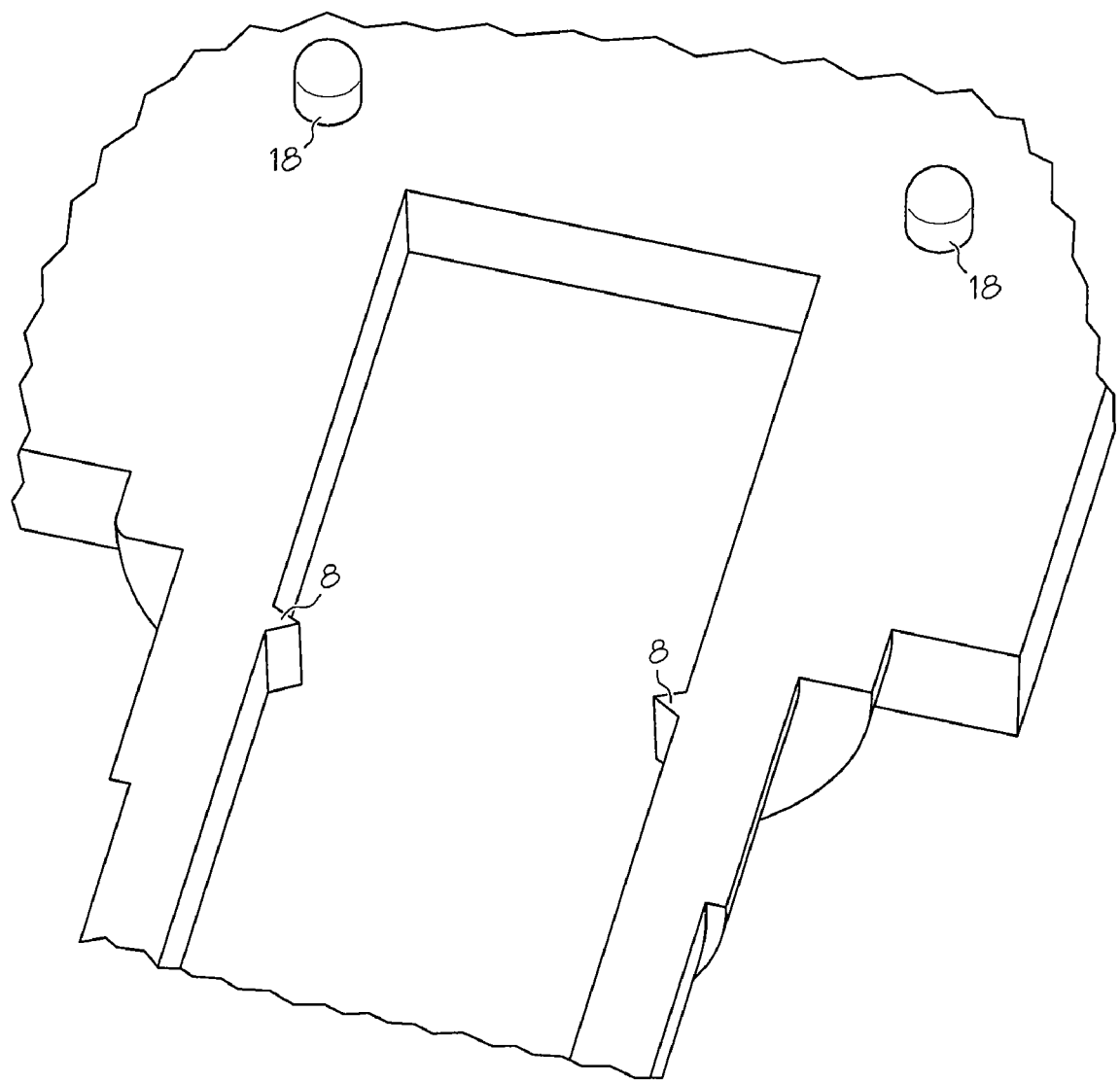
FIG. 3 is an enlarged isometric view of the holder 2.
Figure 4:
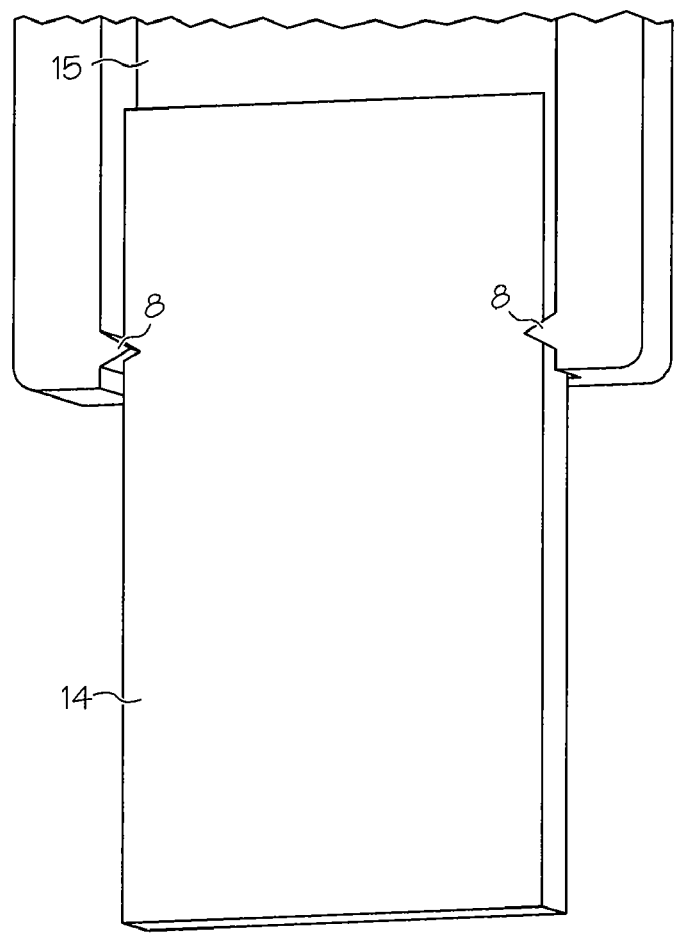
FIG. 4 is an enlarged view of the holder.
Figure 5:
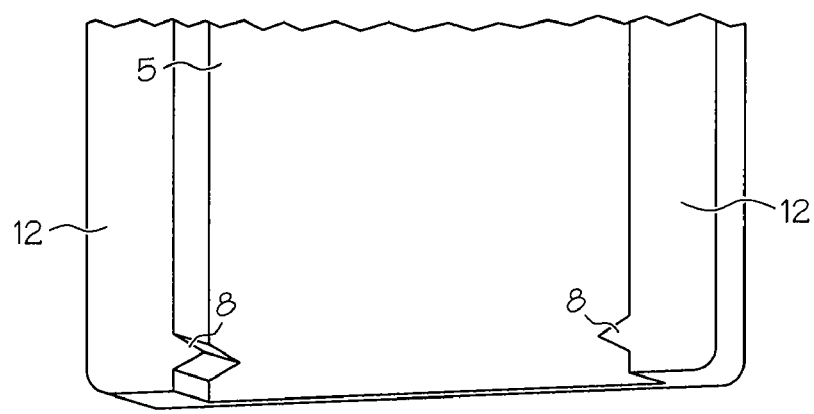
FIG. 5 is an enlarged view of the holder.
Figure 7:
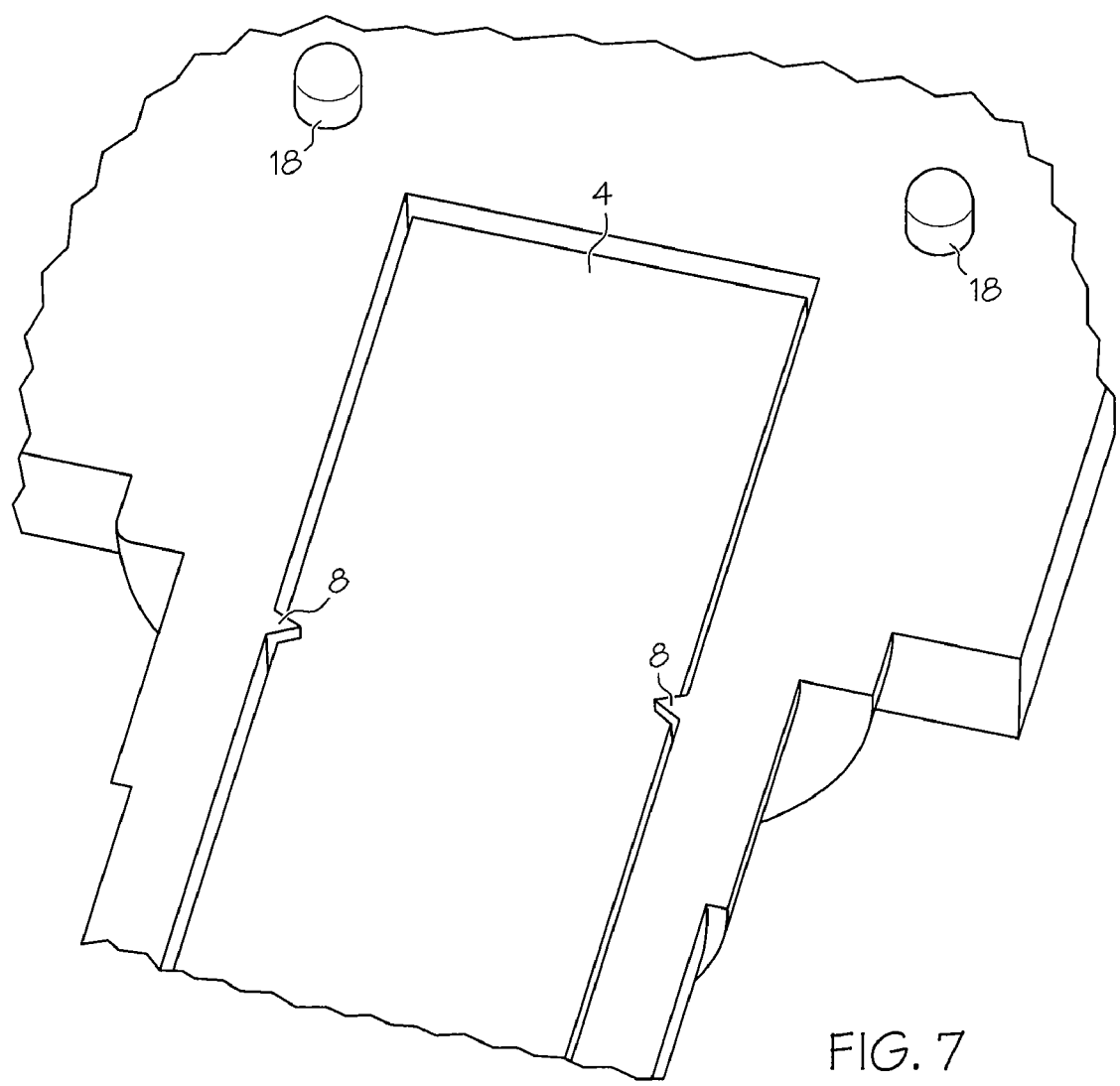
FIG. 7 is an enlarged view of the holder in FIG. 2.

The holder 2 is preferably manufactured as a single piece using standard techniques. For example, it can be injection molded, compression molded or machined. The holder 2 may include complimentary, interlocking engagement features 18 as depicted in FIGS. 2, 3, and 7. The holder is shown in an open or unassembled position in FIG. 2. The holder 2 may be formed from any suitable material that will withstand the environment of the sample, diluent, labeling reagents, and any additional reagents that may be added to the receptacle 3. Preferably, it is made of plastic or the like, more preferably, polypropylene, polystyrene or the like.

As depicted in FIGS. 1-8, the holder 2 has an elongated portion 6. The elongated portion 6 may further comprise an alignment feature 5, one or more retention features 8, and shield regions 12. The holder 2 may further comprise secondary pins 19 (shown in FIG. 6). Upon folding the unassembled holder at the hinge 7 shown in FIG. 2, an assembled holder 2 (as shown in FIGS. 1 and 8, shown with test strip 4) is formed. In one embodiment, folding the top portion of the grip member upon the lower portion of the grip member at the hinge region forms the grip member 11 and the closure 10.

The grip member 11 of the holder comprises a top portion and lower portion separated at the hinge 7. The hinge 7 may be a living hinge. A living hinge is a hinge or flexure bearing with no moving parts, generally a thin section of plastic or other material that connect two segments of a part to keep them together and allows movement. The grip member 11 comprises a top portion and a bottom portion. The top portion is folded over or snapped into place on the lower portion at the hinge to capture the upper edge of a test strip. When the top portion and lower portion of the grip member 11 are aligned, the test strip is secured in place. It will also be understood by one of ordinary skill in the art that the hinge 7 is not essential, such that the holder 2 may be manufactured by two separate pieces, one piece identical to the portion below the hinge 7, the other piece identical to the portion above the hinge 7.

Figure 6:
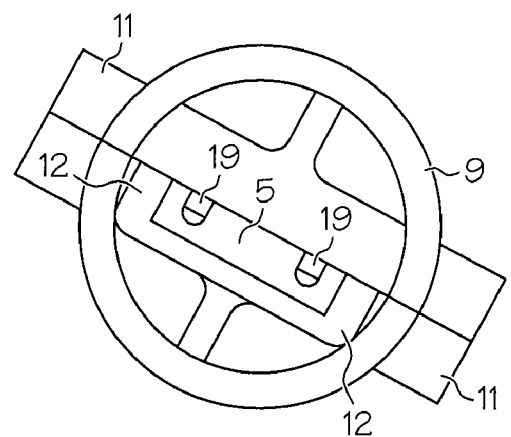
FIG. 6 is a bottom view of the holder in FIG. 2.

Once folded, the holder 2 has a general shape of that depicted in FIGS. 1 and 8. To assemble the holder 2 as shown in FIGS. 1 and 8, a lateral flow test strip 4 or the like is first placed within the alignment feature 5. In a preferred embodiment, the alignment feature 5 may be a recess with a solid wall on each side or a periodic wall (for example, guide posts, or serial guides, formed in the elongated portion 6 of the holder 2. Upper and lower retention features 8 (shown in a close-up view in FIGS. 3, 4, and 7) may be present to secure the second and first absorbent pads, respectively. The holder 2 is folded at a hinge 7, thereby capturing the upper edge of the test strip 4. Secondary pins 19, as shown in FIG. 6 (bottom view of holder without a test strip) may also be provided. The secondary pins 19 may be present to further secure the test strip 4 in place by locking into the second absorbent pad 17. In one embodiment, the secondary pins 19 secure the test strip by penetrating into the second absorbent pad approximately ½ mm.

The assembled holder 2 as shown in FIG. 8 may further comprise a stop feature 9. The stop feature 9 is formed upon assembling the top portion and the lower portion of the holder 2 together at the hinge 7. In one embodiment, best viewed in FIG. 8, the stop feature 9 is comprised of a ledge-like region that extends outward from the closure 10. The stop feature 9 prevents holder 2 from being inserted into the receptacle 3 beyond a fixed point. The stop feature 9 positions the distal end of the holder 2 and the test strip 4 in the proper position within receptacle 3 relative to the sample, at a distance necessary for initiation of the reaction, but such that the lower edge of test strip 4 contacts the sample but the lower edge of the holder 2 does not contact the test sample. The stop feature 9 and alignment feature 5 are in relation to one another such that appropriate positioning of the test strip 4 relative to the sample is achieved when the holder is placed in the receptacle 3.

The assembled holder further comprises a closure 10 (as shown in FIGS. 1 and 8) for the receptacle 3. The closure 10, in one embodiment, is generally plug-like in shape, though any suitable shape that substantially seals the receptacle 3 is contemplated within the present invention. The closure 10 is shaped such that it substantially seals the device 1 when inserted into receptacle 3. The closure 10 shown in FIG. 8 has hollowed-out portions that facilitate manufacturing of the device, though it will be readily understood that the invention is not limited to this embodiment, and the closure 10 may take a variety of different forms.

The assembled holder 2 further comprises a grip member 11. In the embodiment shown in FIGS. 1 and 8, the grip member 11 has a generally rectangular shape. However, the grip member 11 need not have this particular shape, but may have any other shape that allows easy handling of the holder 2. For example, the grip member 11 may have rounded edges, or may also comprise raised ribs, ridges or other texture to facilitate removal and insertion of the holder 2. The grip member 11 is sized such that a user may manipulate and use the holder 2.

As seen in FIG. 2, the holder 2 may also have shield regions 12 that help prevent contamination of the test strip 4 when inserting holder 2 into receptacle 3. In this embodiment, the shield regions 12 may be raised edges on the elongated support 6 that shield the sides of a test strip 4. These raised edges can be a solid wall, as shown, or a broken wall. In use, it is necessary for the user to insert the holder 2 inside the receptacle 3 to initiate the reaction. Liquid or other contaminants may exist on the rim of the receptacle 3. Shield regions 12 protect the test strip 4 from rim contamination when inserted into the receptacle 3.

As shown in FIGS. 1 and 8, the elongated portion 6 may also have one or more "detection guides" 13 to show the user where labeling reagent should accrue. For example, one or more visible marks may be made on a shield region 12 of the test strip or on the elongated portion 6 that corresponds to a region on the test strip 4 that contains a binding reagent for the analyte. The detection guides 13 may be a line or other demarcation, and may be indicated by color or a raised portion of the holder 2. In one embodiment, there are at least three reading lines, corresponding to a detection region for influenza A, a detection region for influenza B and a control line. However, it will be readily understood to one of ordinary skill in the art that the detection guides 13 may take a variety of different forms and may correspond to one or more different analytes and control regions.

The Test Strip

The holder 2 of the present invention may be used to hold any test strip used in the art. In one embodiment, a lateral flow assay test strip as known in the art (and depicted in FIGS. 1, 2 and 8) is placed in the holder 2. The test strip 4 may use the one-step or two-step method. In the one-step method, the test strip 4 has a first labeling reagent diffusively immobilized in the first absorbent pad 14. In the two-step method, as described above, the first labeling reagent is separate from the test strip 4. In a two-step embodiment, a labeling reagent such as a dried conjugate is provided in the receptacle 3 separately from the test strip 4. The labeling reagent may also be added by the end-user.

In embodiments using a lateral flow test strip, the test strip 4 can be any lateral flow test strip known in the art. For example, the test strip 4 preferably is comprised of a first absorbent pad 14, a membrane 15, and a second absorbent pad 17, as shown in FIGS. 1, 2 and 8. FIG. 1 depicts a test strip 4 placed in the device, and FIG. 2 depicts the test strip prior to placing in the holder 2 of the device 1. Referring to FIG. 2, suitable labeling reagents comprising a first binding reagent and a label may be impregnated in the first absorbent pad 14, and suitable second binding reagents are impregnated in the membrane 15. The binding reagents are selected based on the analyte to be detected, and suitable selection of binding reagents will be readily understood by one of ordinary skill in the art. The second binding reagents impregnated in the membrane 15 form one or more "detection region(s)" 16 further comprising regions containing second binding reagents for the analyte and/or "control regions." Suitable reagents for control regions will be readily understood by one of ordinary skill in the art. The test strip 4 may have one or more detection regions for analyte and one or more control regions, as desired.

The test strip 4 used with the device 1 may also be any other strip known in the art and compatible with the holder 2 as described above, and is not limited to test strips for lateral flow immunoassays. For example, the present invention may employ a membrane used for thin layer chromatography. In such an embodiment, the thin-layer chromatography membrane comprises an appropriate membrane or other material affixed to the elongated portion 6 of the holder 2. The sample, either liquid or a solid dissolved in a volatile solvent, is deposited in the receptacle 3 of the device 1 or directly on the test strip 4. The constituents of a sample can be identified by simultaneously running standards with the unknown. The solvent containing sample moves up the elongated portion 6 of the holder 2 or the membrane/test strip 4 contained thereon by capillary action. When the solvent front reaches the upper edge of the holder 2, the separated spots may be visualized using appropriate detection methods such as ultraviolet light or placing the plate in iodine vapor. The different components in the mixture move up the plate at different rates due to differences in their partitioning behavior between the mobile liquid phase and the stationary phase.

Where the device 1 is used in combination with a lateral flow assay test strip 4, the test strip 4 is assembled as understood in the art. FIG. 2 depicts an example of a lateral flow test strip 4 that may be used. In one embodiment, the immunoassay test strip comprises a bibulous membrane strip 15 such as nitrocellulose, a first absorbent pad 14, and a second absorbent pad 17. "Bibulous" materials include untreated forms of paper, nitrocellulose and the like which effect chromatographic separation of components contained in liquids which are passed therethrough. In contrast, in "nonbibulous" liquid flow all of the dissolved or dispersed components of the liquid which are not permanently entrapped or 'filtered out' are carried at substantially equal rates and with relatively unimpaired flow though the membrane or support. Bibulous flow results in preferential retention of one or more components. Test strips as disclosed in Charlton, et al., U.S. Pat. No. 5,989,921 "Test Device and Method for Colored Particle Immunoassay" issued Nov. 23, 1999, incorporated herein by reference may be used.

In embodiments using a lateral flow test strip, the membrane is generally a porous carrier such as nitrocellulose. The test strip 4 may further comprise a backing layer, such as Mylar, or may be directly adhered to the elongated portion 6 of the holder 2. The test strip 4 may have a backing of one continuous piece of laminate or separate pieces. The backing may also be a laminate such as vinyl but one skilled in the art will recognize that numerous materials can be used to provide support to the test strip. In embodiments where the test device is used with methods other than the lateral flow immunoassay, the strip may comprise chromatographic paper or other materials suitable for the type of assay desired.

First Absorbent Pad

In embodiments of the present invention using a lateral flow assay test strip, a first absorbent pad is preferably used. Referring to FIG. 2, the first absorbent pad 14 is placed at the end of the membrane 15 where the sample is to be contacted with the strip, typically at the distal end furthest from the holder. The first absorbent pad 14 contacts the sample when the holder 2 is inserted into the receptacle 3. The first absorbent pad 14 may extend beyond the lower edge of the holder 2 such that sample contacts the test strip 4 without contacting the lower edge of the holder 2. This first absorbent pad 14 extends into the sample volume when the holder 2 is secured in the receptacle 3. Positioning of the first absorbent pad 14 relative to the sample and the receptacle 3 is fixed via the alignment feature 5 and the stop feature 9 of the holder 2. Contact of the pad 14 to sample or sample-diluent initiates the assay by permitting the pad 14 to absorb sample, conducting flow along the membrane 15. Flow along the membrane 15 permits analyte in the sample to contact second binding reagents immobilized on the membrane. The first absorbent pad 14 can further serve as a filter for separating liquid sample from particulate matter that could interfere with capillary flow, further reducing the possibility of false positives.

Absorbent pads used with lateral flow immunoassays are well known in the art. Non-limiting examples of pads that may be used with the present invention include Whatman D28, Whatman 1.5WF, Whatman 3MM CHR, available from Ahlstrom, 122 West Butler Street, Mount Holly Springs, Pa. 17065, or Whatman, 200 Park Ave., Florham Park, N.J. 07932.

Matrix Strip

Again referring to FIG. 2, the matrix strip is a porous membrane 15 that may be any suitable membrane known in the art. In general, the porous membrane 15 may be made from any of a variety of materials through which the detection probes are capable of passing. For example, the materials used to form the porous membrane 15 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like.

The pore size of the membrane 15 may preferably be about 0.05 to about 20 microns.

In embodiments using a lateral flow immunoassay, the test strip 4 further comprises one or more detection regions 16, as described above, and as shown in FIGS. 1, 2, and 8. The test strip 4 may further comprise one or more control zones, as desired by the user. The one or more detection regions 16 comprise binding reagents impregnated on the matrix strip at predetermined points.

The detection regions 16 comprise unlabeled binding reagents immobilized in the membrane 15 that bind to the analyte-labeling reagent complex. Accumulation of bound analyte results in a visible signal. The control region is comprised of immobilized reagents that typically bind to a region of the labeling reagent (such as the Fc region of the first labeling reagent, where the first labeling reagent is an antibody) and accumulated labeling reagent at the control region indicates successful completion of the assay.

The one or more detection regions 16 may contain the same binding reagents, or may contain different binding reagents for capturing multiple analytes. For example, the detection region 16 may include two or more distinct binding regions (e.g., lines, dots, etc.) for the detection of one or more analytes and one or more control regions for confirmation of assay completion and integrity. Preferably, the binding and control regions may be disposed in the form of lines in a direction that is substantially perpendicular to the flow of the test sample through the device 1. However, in some embodiments, the binding and control regions may be disposed in the form of lines in a direction that is substantially parallel to the flow of the test sample through the assay device.

The control region is generally located at a site on the membrane 15 downstream from the detection regions that contain binding reagents specific to analyte. The reagent may bind to both complexed and uncomplexed conjugate particles, and is therefore generally different from the first binding reagent. In one embodiment, the reagent is a biological binding reagent (e.g., antigens, haptens, protein A or G, neutravidin, avidin, streptavidin, primary or secondary antibodies (e.g., polyclonal, monoclonal, etc.), and complexes thereof) that is different than the first binding reagent. For example, the first binding reagent may be a monoclonal antibody while the second binding reagent may be avidin (a highly cationic 66,000-dalton glycoprotein), streptavidin (a non-glycosylated 52,800-dalton protein), neutravidin (a deglysolated avidin derivative), and/or captavidin (a nitrated avidin derivative). In this embodiment, the second binding reagent may bind to biotin, which is biotinylated or contained on detection probes conjugated with a monoclonal antibody different than the monoclonal antibody of the first binding reagent.

In addition, various non-biological materials may be used for the second binding reagent of the control region as are known to one of ordinary skill in the art.

Second Absorbent Pad 17

Where lateral flow immunoassay test strips are employed such as those depicted in FIGS. 1, 2 and 8, the test strip 4 also comprises a second absorbent pad 17. The first absorbent pad 14, membrane 15, and second absorbent pad 17, as described above, comprise a flow path for the liquid containing the analyte to be detected. The second absorbent pad 17 serves as a reservoir for collection of sample liquid that has passed through the membrane 15 via capillary action. Suitable sorbents include commercial types available, for example, from Alstrom or Whatman.

In one embodiment, the test strip 4 employs a qualitative, rapid, lateral-flow immunoassay as described above, wherein the analytes to be detected are influenza A and influenza B viral nucleoprotein antigens in human nasal wash, nasopharyngeal aspirate, throat swab, or nasal and nasopharyngeal swab samples. In this embodiment, the membrane 15 is comprised of nitrocellulose and further comprises two separate detection regions further comprising dried monoclonal or polyclonal antibodies (second binding reagents) for influenza A and influenza B. A first detection region comprises antibodies to influenza A, and a second detection region comprises antibodies to influenza B. The antibodies are immobilized in the membrane. When analyte conjugated to the first labeling reagent binds to antibody immobilized in the test strip 4, a visibly detectable reaction occurs. Where colloidal gold is used as the label, the detection region becomes a pink to red color. In this embodiment, any suitable antibody may be used at the control region. In one embodiment, the antibody used is goat anti-mouse antibody, which is then immobilized at the control region of the test strip 4.

Labeling Reagent (Conjugate)

Where a lateral flow immunoassay test strip is employed, a suitable labeling reagent is selected. Depending on the method chosen, a predetermined amount of at least one type of labeling reagent is deposited in the receptacle 3, impregnated in the first absorbent pad 14, or provided separately to the end-user.

The labeling reagent used may be any particle, protein or molecule that recognizes or binds to the analyte in question, having attached, conjugated or otherwise bound a detectable label. The exact nature of the labeling reagent depends on whether the assay uses the competitive or sandwich type assay.

In one embodiment, the particle, protein or molecule is a natural or non-natural monoclonal or polyclonal antibody. Polyclonal and monoclonal antibodies or fractions thereof having specific binding properties and high affinity for virtually any antigenic substance are known and commercially available or can be produced from stable cell lines using well known cell fusion and screening techniques.

The labeling reagent of the present invention may be lyophilized, freeze-dried or the like, and placed in the receptacle 3. In one embodiment, the labeling reagent may be lyophilized onto a glass fiber or other suitable pad. The labeling reagent may contain additional cryoprotective agents or meta-soluble proteins as described in Ching et al, U.S. Pat. No. 6,534,320. Where the reagent is stable in a liquid form, the reagent need not be lyophilized. The quantity of the labeled reagent is calculated or experimentally optimized for achieving the desired assay sensitivity.

In one embodiment, the labeling reagent comprises one or more antibodies, for example, influenza A or B antibodies, conjugated to gold. In another embodiment, the labeling reagent is manufactured as a eLyoSphere™ by Biolyph LLC 1317 Fifth Street South, Hopkins, Minn. 55343-7807 USA. In this embodiment, one or more antibodies (for example, antibodies to influenza A antibody-1) are conjugated to gold and provided in a liquid state in Gold Conjugate Dry Buffer. The gold conjugate dry buffer comprises Tris, Sodium Citrate, Sucrose, EDTA, Sodium Azide, and Triton X-405. Microliter aliquots of liquid are then lyophilized as a precise and durable unit in the form of a sphere. The LyoSpheres™ are dispensed at the precise volume required in aliquots ranging from 13 μL to 250 μL. If more volume per device is required, multiple LyoSpheres™ can easily be packaged inside a single device. In one embodiment, the LyoSphere™ spheres comprise approximately about 15-50 microliters or about 25-30 microliters each.

The LyoSpheres™ are packaged inside the receptacle 3 immediately after manufacture. The receptacle 3 may be vacuum sealed and packaged with a desiccant to prevent degradation. Lyophilized reagents are handled inside packaging suites operating at below 2% relative humidity (RH).

Labels

Where a label is required for detection of results, any substance generally capable of generating a signal that is detectable visually or by an instrumental device may be used. Non-limiting examples of suitable substances include chromogens, catalysts, luminescent compounds (e.g., fluorescent, phosphorescent, etc.), radioactive compounds, visual labels including colloidal metallic (e.g., gold) and non-metallic particles, dyed particles, enzymes or substrates, or organic polymer latex particles, liposomes or other vesicles containing signal producing substances, and the like. See for example, U.S. 2005/112703, Song et al. and U.S. 2006/0127886, Kaylor et al.

Metal sols and other types of colored particles useful as labels in immunoassay procedures are known and commonly used in the art for lateral flow immunoassays. See for example, Ching et al, U.S. Pat. No. 6,534,320 for a description of colloidal particles suitable as labels, incorporated herein by reference. See also U.S. Pat. No. 4,313,734 and U.S. Pat. No. 6,485,982.

In some embodiments, enzymes may be used as labels. Non-limiting examples of enzymes suitable for use as detection probes are disclosed in U.S. Pat. No. 4,275,149. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable labels may be described in U.S. Pat. Nos. 5,670,381 and 5,252,459. In some embodiments, the label may contain a fluorescent compound that produces a detectable signal. The fluorescent compound may be a fluorescent molecule, polymer, dendrimer, particle, and so forth. Some examples of suitable fluorescent molecules, for instance, include, but are not limited to, fluorescein, europium chelates, phycobiliprotein, rhodamine and their derivatives and analogs.

The labels, such as described above, may be used alone or in conjunction with a microparticle (sometimes referred to as "beads" or "microbeads"). For instance, naturally occurring microparticles, such as bacteria, polysaccharides (e.g., agarose), and so forth, may be used. Further, synthetic microparticles may also be utilized. For example, latex microparticles that are labeled with a fluorescent or colored dye may be used. Although any latex microparticle may be used in the present invention, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable microparticles may be described in U.S. Pat. Nos. 5,670,381 and 5,252,459. Commercially available examples of suitable fluorescent particles include fluorescent carboxylated microspheres sold by Molecular Probes, Inc., 29851 Willow Creek Road, Eugene, Oreg. 97402 USA under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, non-limiting commercially available examples of suitable colored, latex microparticles include carboxylated latex beads sold by Bang's Laboratory, Inc., 9025 Technology Drive, Fishers, Ind. 46038-2886.

When used, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 1 nanometer to about 100 microns, and in some embodiments, from about 10 nanometers to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 80 nanometers, in some embodiments from about 0.1 to about 5 nanometers, and in some embodiments, from about 1 to about 20 nanometers.

In some instances, it is desired to modify the particles in some manner so that they are more readily able to bind to the analyte. In such instances, the particles may be modified with certain specific binding members that are adhered thereto to form conjugated particles. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and binding nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the particles using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the particle may contain a relatively high surface concentration of polar groups. In addition, although conjugate particles are often functionalized after synthesis, in certain cases, such as poly(thiophenol), the microparticles are capable of direct covalent linking with a protein without the need for further modification.

In some embodiments, the first or second binding reagent may be a biological binding reagent. Such biological binding reagents are well known in the art and may include, but are not limited to, antigens, haptens, protein A or G, neutravidin, avidin, streptavidin, captavidin, primary or secondary antibodies (e.g., polyclonal, monoclonal, etc.), and complexes thereof. In many cases, it is desired that these biological binding reagents are capable of binding to a specific binding member (e.g., antibody) present on the conjugate particles.

It may also be desired to use various non-biological materials for the first or second binding reagent. For instance, in some embodiments, the reagent may include a polyelectrolyte. The polyelectrolytes may have a net positive charge or a negative charge, or a net charge that is generally neutral. Some suitable examples of polyelectrolytes having a net positive charge include, but are not limited to, polylysine (commercially available from Sigma-Aldrich Chemical Co., Inc., St. Louis, Mo.), polyethylenimine; epichlorohydrin-functionalized polyamines and/or polyamidoamines, such as poly (dimethylamine-co-epichlorohydrin); polydiallyldimethylammonium chloride; cationic cellulose derivatives, such as cellulose copolymers or cellulose derivatives grafted with a quaternary ammonium water-soluble monomer; and so forth. In one embodiment, CelQuat® SC-230M or H-100 (available from National Starch & Chemical, Inc. 742 Grayson Street, Berkeley, Calif. 94710-2677), which are cellulosic derivatives containing a quaternary ammonium water-soluble monomer, may be utilized. Some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be used. Some of these, such as amphiphilic polyelectrolytes (i.e., having polar and non-polar portions) may have a net charge that is generally neutral. For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

Diluent

The diluent may be provided in a separate container such as a vial or in a closed pipette.

The diluent used with the present invention may be supplied by the end-user or supplied as part of a kit, in a concentrated or ready-to-use formulation. The diluent may be added before or after the addition of sample, and may be added regardless of whether a one-step method or two-step method is used, where the test strip 4 is a lateral flow immunoassay. One purpose of the diluent is to re-suspend and carry the conjugate particles. The diluent may be any liquid that will sufficiently solubilize and resuspend the labeling reagent such that binding and subsequent labeling of the analyte of interest will occur in the solution. The diluent must also be capable of carrying the labeling reagent-analyte complex via capillary action along the wicking membrane 15 and across the detection regions 16. Diluent can also serve the added benefit of decreasing the amount of body fluid required.

Assay performance may be optimized by limiting the total volume of sample and diluent in the receptacle 3 to a level such that liquid contacts the first absorbent pad 14 without contacting the elongated portion 6 of the holder 2. Contact of the diluent-sample solution with the elongated portion 6 of the device 1 permits undesired wicking of the solution between the test strip 4 and holder 2. Wicking behind the test strip 4 interferes with the proper flow of the solution along the test strip 4. As such, the level of solution is preferably restricted to a level below the bottom edge of the holder 2, which can be achieved via either or both the alignment feature 5 and stop feature 9 of the holder 2 of the device 1.

Examples of suitable diluents include phosphate buffered saline (PBS) solution (pH of 7.2), tris-buffered saline (TBS) solution (pH of 8.2) or 2-(N-morpholino) ethane sulfonic acid (MES) (pH of 5.3). These may contain other additives to aid the performance of the assay, such as polyethylene glycol, proteinaceous materials such as gelatin, casein, and bovine serum albumin, detergents such as sodium dodecyl sulfate, sodium deoxycholate, and TRITON X-100 (polyethylene glycol tert-octylphenyl ether), water-soluble polymers, and preservatives. In one embodiment, the diluent may comprise about 10 to about 13 g/L, or about 12.1 g/L Tris-base; about 0.9 to about 2.0 g/L, or about 1.86 g/L EDTA; about 5 to about 15 g/L, or about 10.00 g/L BSA; about 1 to about 3 mL/L, or about 2.0 mL/L Thesit; about 0.94 g/L Sodium azide; about 8.5 to about 30 g/L, or about 29.22 g/L sodium chloride; about 8 to about 30 g/L, or about 25 g/L CHAPS; about 0.32 mL/L Gentamicin (50 ug/mL) adjusted to a pH of about 7 to about 9. In one embodiment, the pH is about 9.0.

Method of Use

Test Sample

As described above, the test sample used may be derived from various sources. The sample used depends in part on the availability of the sample and the analyte to be detected. The sample may be processed prior to use with the device described herein. Contemplated samples that may be used with the present invention include, but are not limited to, swabs of oral or nasal mucosa, urine samples, nasal wash, nasopharyngeal aspirate, throat swab or the like.

Analytes

The device described herein is suitable for any analyte for which a suitable binding partner is available and which is capable of migrating along a strip with the liquid sample via lateral flow. Exemplary analytes are described above, and are understood to one of skill in the art.

The device may be used with lateral flow immunoassay test strips that employ either the one-step or two-step method as described above. For example, in one embodiment of the present invention, the labeling reagent used may be impregnated on the first absorbent pad 14 of the test strip 4, thus employing the "one-step" method. The user may directly apply, contact or deposit the test sample to the first absorbent pad 14. Diluent may be added before or after sample is contacted with the test strip 4. The diluent may be applied to the receptacle 3 by a separate source such as by pipette or any other effective means known to those skilled in the art. The diluent travels through the first absorbent pad 14 that is in liquid communication with the porous membrane 15, to one or more detection regions 16. In this embodiment, the labeling reagent need not be pre-dispensed into the receptacle 3. Further, in this embodiment, the holder 2 containing the test strip 4 may be provided to the consumer already fitted inside the receptacle 3.

Alternatively, the device 1 may be used with lateral flow immunoassay test strips that employ the two-step or "pour on" method. In this embodiment, a sample is first mixed with a labeling reagent prior to contacting the sample to a test strip 4. The sample and labeling reagent may be mixed inside the receptacle 3, or in a separate container. The holder 2 containing the test strip 4 is then contacted with the mixture containing sample and labeling reagent.

In one embodiment employing the two-step method, the labeling reagent is provided pre-dispensed in a receptacle 3. The receptacle 3 may be provided to a consumer containing the labeling reagent and sealed with a cap, plug or similar closure. In this embodiment, the labeling reagent may be provided in a variety of forms, including, for example, dried onto receptacle 3, dried into pellet, dried into a powder, vacuum dried, freeze dried, forced air-high temperature dried, lyophilized using standard methods, or lyophilized into spheres as described below. The labeling reagent may further be lyophilized onto a glass fiber or other suitable pad, or may be dried onto the bottom of the receptacle 3. The user may then open the receptacle 3 and add diluent to solubilize the labeling reagent, or the labeling reagent may be solubilized, where necessary, with the addition of sample. Diluent may be added before or after sample is placed in the receptacle 3.

The user, regardless of the type of test strip 4 used, initiates lateral flow along the test strip 4 by inserting the holder 2 containing a suitable test strip 4. The holder 2 and test strip 4 may be assembled prior to providing the device 1 to the consumer, or the holder 2 and test strip 4 may be provided separately for assembly prior to use.

Upon inserting the holder 2 containing a suitable test strip 4 into the receptacle 3 containing the sample, lateral flow is initiated. In embodiments using a lateral flow immunoassay-type test strip, the sample and/or diluent travels through the first absorbent pad 14 in liquid communication with the porous membrane 15 having one or more detection regions 16. Liquid sample and/or diluent then accumulates in the second absorbent pad 17.

Detecting Test Results

A variety of labels may be used with the present invention as discussed above. The type of label used to determine the manner in which the label is detected. Non-limiting examples of label detection that may be used with the device are set forth below.

Colored Particles

Colored particles such as a metal sol (for example, colloidal gold) may be used, especially in embodiments utilizing lateral flow immunoassays. In embodiments using these types of labels, color development at the reaction zone may be visually observed without the aid of additional instrumentation. Where a control region is present, presence or absence of color at the control region indicates whether the test was successfully completed. For example, where no line appears at the control region, it may be concluded that the test is inconclusive, whether as a result of reagent degradation or insufficient sample. Where the reaction is quantitative in nature, color development may be compared with the color of one or more standards of internal controls to determine the approximate level of analyte concentration. Any suitable colored particle known in the art may be employed with the present invention, and such particles will be known to one of ordinary skill in the art.

Luminescent Labels

An alternative to colored particles as labels are those labels using luminescence. Visually read assay systems using colored labels such as gold sol or blue latex particles may provide only limited sensitivity.

A technique known as "time-resolved fluorescence detection" may also be used in the present invention. Time-resolved fluorescence detection is designed to reduce background signals from the emission source or from scattering processes (resulting from scattering of the excitation radiation) by taking advantage of the fluorescence characteristics of certain fluorescent materials, such as lanthanide chelates of europium (Eu (III)) and terbium (Tb (III)). Chelates may exhibit strongly red-shifted, narrow-band, long-lived emission after excitation of the chelate at substantially shorter wavelengths. Typically, the chelate possesses a strong ultraviolet absorption band due to a chromophore located close to the lanthanide in the molecule. Subsequent to light absorption by the chromophore, the excitation energy may be transferred from the excited chromophore to the lanthanide. This is followed by a fluorescence emission characteristic of the lanthanide. The use of pulsed excitation and time-gated detection, combined with narrow-band emission filters, allows for specific detection of the fluorescence from the lanthanide chelate only, rejecting emission from other species present in the sample that are typically shorter-lived or have shorter wavelength emission.

Fluorescence detection may be used to detect the presence of analyte in the detection and control zones and generally utilizes wavelength filtering to isolate the emission photons from the excitation photons, and a detector that registers emission photons and produces a recordable output, usually as an electrical signal or a photographic image. Examples of the types of detectors include spectrofluorometers and microplate readers; fluorescence microscopes; fluorescence scanners; and flow cytometers. One suitable fluorescence detector for use with the present invention is a FluoroLog III Spectrofluorometer, which is sold by SPEX Industries, Inc. of Edison, N.J. Label in the binding zone may be confined to one or more discrete binding regions.

The luminescent label determinable by any of the subject assay readers may be a fluorescent label, such as those described in US App. 2004/0151632, Badley, et al. In such embodiments, the emission signal may be a fluorescent emission signal. In certain embodiments, the light source may be an ultra-violet light source. The excitation signal may be ultra-violet light in certain embodiments.

Radioactive Labels may also be used, and detection is achieved using standard methods as known in the art. The holder 2 may or may not be removed for detection of radioactive labels.

EXAMPLES

Example I

The following examples relate to an embodiment using the device 1 wherein the test strip 4 is a rapid, qualitative, lateral-flow immunoassay for detecting both influenza A and influenza B viral nucleoprotein antigens in samples such as human nasal wash, nasopharyngeal aspirate, throat swab, and nasal or nasopharyngeal swab samples.

Test Kit and Components

A test kit for detection of Influenza A and B is prepared, comprising a test tube shaped receptacle 3, a holder 2, sample diluent, and instructions. The receptacle 3 contains a lyophilized bead of colloidal gold linked monoclonal antibodies to influenza A and influenza B ("detector antibodies"). The holder 2 carries a nitrocellulose membrane 15 with dried capture antibodies at separate lines for influenza A and influenza B. The holder 2 is engaged with the receptacle 3 during testing and subsequent disposal to reduce exposure to potential pathogens. The holder 2 also provides one or more detection guides 13 for the test strip 4.

The kit includes a test strip 4 with a holder 2 assembled as shown in FIG. 8 enclosed in a foil pouch with a desiccant and a desiccant indicator that is used to indicate moisture levels inside the foil pouch. The test strip 4 carries monoclonal anti-influenza A and influenza B capture antibodies for the test lines and a goat anti-mouse antibody for a control. The influenza strains used to produce the monoclonal antibodies incorporated into the test strip 4 and labeling reagents are A/Texas, A/H1N1, B/Singapore and B/Beijing/184/93. The holder 2 is used to substantially seal receptacle 3. The elongated portion 6 of the holder 2 prevents the test strip 4 from bending while the receptacle 3 is capped. The test strip 4 is ready to use as supplied. The pouch containing the test strip 4 and holder 3 is stored at 2-25° C. when not in use.

The kit further includes a capped receptacle 3 containing a labeling reagent in the form of a conjugate bead. The receptacle 3 is enclosed in a foil pouch to prevent moisture contamination. The labeling reagent comprises a gold-conjugated anti-influenza A and anti-influenza B which serve as the detector antibodies. The influenza strains used to produce the monoclonal antibodies incorporated into the test strip 4 and labeling reagent are A/Texas, A/H1N1, B/Singapore and B/Beijing/184/93. The foil pouch is stored at 2-25° C. when not in use. The cap closing the receptacle 3 is not removed prior to use.

Sample Diluent/Negative Control

The kit further includes diluent provided in a dropper vial that serves as a negative control. The solution is stored at about 2° C. to about 25° C. when not in use.

Plastic transfer pipettes with 50 uL and 100 uL volume marks are also provided with the kit.

The labeling reagent provided in the receptacle 3 is in the form of a lyophilized bead. The lyophilized bead is a LyoSphere™ bead available from Biolyph. A LyoSphere comprises a blend of three antibodies including influenza A antibody-1, influenza A antibody-2, and influenza B antibody-1 conjugated to gold. It is prepared from a liquid "gold conjugate dry buffer" which is supplied to Biolyph, a company based in Hopkins Minn. and specializing in Life Science & Diagnostic Reagents, http://www.biolyph.com. The gold conjugate dry buffer is comprised of Tris, PEG-20,000, sodium citrate, PVP-40, sucrose (0.5%), BSA, EDTA, non-fat dry milk, sodium azide, tween-20, triton X-405, adjusted to a pH of about 9.0 to about 9.5 Approximately 25-30 microliters is dried into a single bead.

The nitrocellulose membrane 15 for the test strip 4 is prepared in the following manner: First, appropriate binding reagents as described herein are applied to the nitrocellulose in the presence of a "test/control line buffer" comprising sodium phosphate, sodium chloride, and sodium azide. The nitrocellulose is then air dried in a heat tower for several minutes. A "block buffer," comprising sodium phosphate, tween-20, sodium chloride, triton X-405, BSA, sodium azide, and non-fat dry milk, is applied to the nitrocellulose. The nitrocellulose is air dried a second time in a heat tower for several minutes, laminated and cut into test strips. The test strip is assembled, including an adhesive backing, blocked nitrocellulose, upper wicking pad, and lower sample pad. The test strip 4 is assembled in a humidity controlled environment.

The test strip 4 is placed in a pouch with the gold conjugate tubes and desiccant in a humidity controlled environment.

Method of Using the Device

Specimen Collection

Specimens are collected and transported in standard containers and stored at about 2-8° C. until tested. Ideally, the specimen is tested as soon as possible, but may be held up to 72 hours at 2-8° C. prior to testing. If testing cannot be performed within this time frame, specimens may be frozen immediately on receipt and stored frozen (<about −20° C.) for up to two weeks until tested. A single freeze/thaw cycle should not affect test results.

Transport media appropriate to the sample to be analyzed may be used. For example, for the collection of oral fluids, the following transport media are acceptable for collection of specimens: M4, M4-RT, M5, Stuart's, Hank's Balanced Salt, Amies, Dulbecco's PBS, 0.85% saline, available from Fisher Scientific, 4500 Turnberry Drive, Hanover Park Ill. 60133.

The following types of swabs are used (Swab/Handle): cotton/plastic, rayon/plastic, foam/plastic, polyester/metal, polyester/plastic, rayon/metal, cotton/metal, flocked nylon, and the like. Calcium alginate swabs are not preferred because the chemical decreases positive reactions.

Specimen Preparation

Specimens and reagents are first brought to room temperature (20-25° C.) before testing.

Where nasal wash, nasopharyngeal aspirate or swab specimens in transport media are used, the following steps are followed:

1. A receptacle 3 containing labeling reagent is removed from its foil pouch. The receptacle 3 is labeled appropriately.

2. The cap is removed from the receptacle 3.

3. Three drops (approx. 100 μL) of Sample Diluent is added to the receptacle 3 using a dropper vial.

4. Sample is thoroughly mixed regardless of consistency. One of the transfer pipettes supplied with the kit may be used to mix the sample gently but thoroughly by squeezing the pipette bulb three times in the sample. Alternatively, the sample may be mixed for at least 10 seconds using a vortex mixer.

5. Using the same pipette, approximately 100 μl of specimen is drawn and added to the receptacle 3.

6. Using the same pipette, the sample and labeling reagent is thoroughly but gently mixed by squeezing the pipette bulb three times. Alternatively, sample and labeling reagent may be mixed for at least 10 seconds using a vortex mixer. The pipette is then discarded.

Where nasal, throat and nasopharyngeal swab specimens are collected immediately without transport media, the following steps are followed:

1. One receptacle 3 containing labeling reagent is removed from its foil pouch. The receptacle 3 is appropriately labeled.

2. The cap is removed from the receptacle 3 and discarded.

3. Using the dropper vial, 8 drops (approximately 300 μL) of Sample Diluent are immediately added to the receptacle 3. For heavily viscous samples, up to 12 drops (approximately 500 μl) of sample diluent can be added.

4. The swab is then dipped into the receptacle 3 and rotated three times in the liquid. The swab is pressed against the side of the tube as it is removed to squeeze out as much fluid as possible.

Test Procedure

To use the device, the conjugate bead is re-hydrated in the receptacle 3 containing labeling reagent with diluent. Sample is then added as described above. The contents are mixed by swirling the receptacle 3 gently before the holder 2 containing the test strip 4 is added. The test is then incubated at about 20° to about 25° C. (approximately room temperature), permitting influenza A or influenza B antigens in the diluted sample to bind to the corresponding monoclonal antibody-colloidal gold conjugate as the sample moves up the test strip. The second binding reagent, a monoclonal antibody for influenza A is bound to the nitrocellulose membrane at a "test-FLU A" position. When the antigen-influenza A antibody-colloidal gold complex binds to the second binding reagent, a visible pink-red line is created. Similarly, the monoclonal antibody for influenza B is bound to the membrane at a "test-FLU B" position. Binding of analyte to this position results in a pink to red line when it captures antigen-influenza B antibody-colloidal gold complexes. When no antigen is present, no complexes are formed and no pink-red line will appear at either the test FLU A or the test FLU B position of the Test Strip. An internal control line is placed upstream of the FLU A and FLU B positions to determine whether adequate flow has occurred through the test strip during a test run. The control line may be any suitable antibody, as understood by one of ordinary skill in the art. For example, the control line may comprise a goat-anti-mouse antibody, which is bound at the control position of the test strip. A visible pink-red line at the control position of the test strip is present each time a specimen or control is tested, provided the test has functioned properly. If no pink-red control line is seen, the test is considered invalid.

To conduct a test using the device, the following steps are performed:

1. The holder 2 containing a test strip 4, provided in a foil pouch, is removed from the pouch.

2. The elongated portion 6 of the holder 2 containing the test strip 4 is inserted into the receptacle 3 containing sample and rehydrated colloidal gold conjugated to Influenza A and Influenza B antibodies (the labeling reagent).

3. The holder 2 is firmly pressed down to substantially seal the receptacle 3.

4. The device 1 is then incubated at 20-25° C. for 15 minutes.

5. The results may then be read within 1 minute. The holder 2 may be removed from the receptacle 3 if the test results are difficult to read. The receptacle 3 may be recapped with the holder 2 or other cap and discarded when testing is completed.

Internal Controls

Internal controls are contained within the test strip 4 and therefore can be evaluated with each test. A pink or red band appearing at the "control line" serves as an internal positive control and indicates that the test has been performed correctly, that sample was added, that it flowed properly, and that the test reagents were active at the time of use. A colorless background around the Control or Test Lines serves as a negative control. A background that obscures the reading of results invalidates the test and is an indication of reagent deterioration, inappropriate sample or improper test performance.

External Control Tests

An external control test may be performed comprising the following steps:

1. All test components, reagents and samples are brought to room temperature (20-25° C.) prior to testing.

2. One receptacle 3 and test strip 4 is used for positive control testing and one receptacle 3 and test strip 4 is used for negative control testing.

3. The receptacles 3 is removed from the foil pouch and the tubes are labeled accordingly. The pouches are discarded.

4. The caps are removed from the receptacles 3.

5. Three to five drops (about 90 uL to about 210 uL) of the Positive Control reagent is added to the receptacle 3 marked for the Positive Control.

6. Exactly Three to seven drops (about 120 uL to about 280 uL) of Sample Diluent/Negative Control is added to the to the receptacle 3 marked for the Negative Control 7. The contents of the receptacles 3 are vortexed or mixed for 10 seconds.

8. The holder 2 containing lateral flow test strips 4 as described above are removed from the foil pouches.

9. The holder 2 containing the test strip 4 is added to each receptacle 3. Each receptacle 3 is closed by pressing firmly on the top of the holder 2.

10. Both receptacles 3 are incubated at 20-25° C. for 15 minutes.

11. The results are read within 1 minute.

Reading Results

A negative test result is determined if there is a pink to red band at the control line position only.

A positive test for Influenza A is determined if a pink to red band develops at the control and Flu A positions, with no band present at the Flu B position. The appearance of a Flu A test line, even if very weak, indicates the presence of influenza A antigen. The intensity of the test line may be less than that of the control line.

Positive test result for Influenza B: PINK-RED bands at the Control and Flu B line positions. No bands at the Flu A test line. The appearance of a Flu B test line, even if very weak, indicates the presence of influenza B antigen. The intensity of the Test line can be less than that of the Control Line.

Invalid test results are determine where no band is observed at the designated position for the control line. The test is invalid since the absence of a control band indicates the test procedure was performed improperly or that deterioration of reagents has occurred. Test results are also considered invalid where a pink to red band appears at either the FLU A or FLU B test line positions of the device after 16 minutes of incubation, or a band of any color other than pink to red develops. False positive results may occur if tests are incubated too long. Bands with colors other than pink to red may indicate reagent deterioration.

Example II

In this example, the kit and method are substantially the same as that described in Example I, with the exception of the labeling reagent used. In this example, the labeling reagent is prepared on a pad that is then placed in the receptacle 3, instead of the lyophilized sphere described in Example I.

To prepare the pad containing the labeling reagent, each antibody is conjugated separately by adding the antibody to a colloidal gold solution at the optimal pH and protein concentration determined for each antibody. The gold conjugate is then blocked with BSA and PEG-20,000, then centrifuged. The supernatant is discarded and the gold conjugate pellet is resuspended in gold conjugate dry buffer. The three conjugates are blended together at the proper ratios to ensure appropriate and consistent reactivities. The liquid gold conjugate is then sprayed on a glass fiber pad and air dried using a heat tower. The dried conjugate is cut into 8×10 mm sections and placed in a test-tube shaped receptacle in a humidity controlled environment. The receptacle containing the conjugate pad may then be used following the same protocol as described above in Example I.

What is claimed is:

1. A testing device comprising
a) a receptacle with an open and a closed end,
b) a holder, and
c) a lateral flow test strip,
wherein the holder is comprised of (i) an elongated portion for affixing the test strip to the holder, (ii) a closure that substantially seals the open end of the receptacle when the holder is inserted into the receptacle thus creating a closed test environment, and (iii) a grip member that extends from the open end of the receptacle; and
wherein the test strip is positioned so lateral flow is initiated when the holder is inserted into the receptacle.

2. The device according to claim 1 wherein the holder further comprises a stop feature;
wherein a stop feature positions the distal end of the holder and the test strip in the proper position within receptacle relative to a sample, at a distance necessary for initiating lateral flow.

3. The device according to claim 1 wherein the holder further comprises at least one alignment feature, wherein an alignment feature is a recess with a solid wall on each side or a periodic wall.

4. The device according to claim 1 wherein the holder further has one or more retention members.

5. The device according to claim 1, wherein the test strip comprises a first absorbent pad, a membrane strip and a second absorbent pad defining a flow path for transporting a liquid sample, the test strip having at least one detection region.

6. The device according to claim 1 wherein the holder further comprises a hinge separating a top portion and a lower portion of a grip member, wherein the grip member is formed by folding the top portion of the grip member upon the lower portion of the grip member at said hinge.

7. The device according to claim 1, wherein the holder further comprises at least one shield region along its length.

8. The device according to claim 1 wherein the holder further comprises one or more detection guides.

9. The device according to claim 1 wherein the holder further comprises one or more secondary pins for securing the test strip.

10. A testing device comprising
a) a receptacle with an open and a closed end,
b) a holder, and
c) a lateral flow test strip, wherein the holder is comprised of (i) an elongated portion for affixing the test strip to the holder, (ii) a closure that substantially seals the open end of the said receptacle when the holder is inserted into the receptacle, and (iii) a grip member that extends from the open end of the receptacle;
wherein the test strip is positioned so lateral flow is initiated when the holder is inserted into the receptacle;
wherein the receptacle contains one or more labeling reagent capable of binding with an analyte;
wherein the test strip further comprises at least one test site comprising one or more immobilized binding reagent; and
wherein the test strip is comprised of a first absorbent pad, a nitrocellulose membrane having a plastic backing and a second absorbent pad, having immobilized second binding reagents impregnated therein.

11. The device according to claim 10 wherein the test strip further comprises a diffusively mobilized labeling reagent.

12. The device according to claim 1 wherein the receptacle contains a label conjugated to at least one binding reagent.

13. The device according to claim 12 wherein the label is selected from the group consisting of enzymes, radioisotopes, fluorescent tags, carbon particles, beads, and metal sols.

14. The device according to claim 12 wherein the labeling reagent is a lyophilized sphere.

15. The device according to claim 12 wherein the labeling reagent is lyophilized on a pad and placed in the receptacle.

16. The device according to claim 1 wherein the receptacle is selected from the group consisting of test tubes, square cuvettes, triangular cuvettes, transparent test tubes, transparent cuvettes, opaque test tubes, and opaque cuvettes.

17. The device according to claim 1 wherein the receptacle has one or more viewing windows.

18. The device according to claim 1 wherein the receptacle is curved in such a manner as to allow magnification of its contents.

19. The device according to claim 1 wherein the test strip is a lateral flow test strip comprising an immobilized second binding reagent specific for influenza A, an immobilized second binding reagent specific for influenza B, and a control region.

20. The device according to claim 1 wherein the receptacle contains one or more labeling reagent capable of binding with an analyte;
  wherein the test strip further comprises at least one test site comprising one or more immobilized binding reagent; and
  wherein the test strip is comprised of a first absorbent pad, a nitrocellulose membrane having a plastic backing and a second absorbent pad, having immobilized second binding reagents impregnated therein.

* * * * *